United States Patent
Wasser et al.

(12)

(10) Patent No.: US 6,362,397 B1
(45) Date of Patent: Mar. 26, 2002

(54) FOR HIGHER BASIDIOMYCETES MUSHROOMS GROWN (AS ONE CELL BIOMASS) IN SUBMERGED CULTURES

(75) Inventors: Solomon P. Wasser, Haifa (IL); Sergey V. Reshetnikov, Kiev (UA)

(73) Assignee: Med Myco Ltd., Haifa (IL)

( * ) Notice: Subject to any disclaimer, the term of this patent is extended or adjusted under 35 U.S.C. 154(b) by 0 days.

(21) Appl. No.: 09/419,206

(22) Filed: Oct. 15, 1999

(51) Int. Cl.[7] ............................................... A01H 15/00
(52) U.S. Cl. ............................... 800/297; 47/1.1; 71/5; 426/7; 260/112.5
(58) Field of Search ................... 47/1.1; 71/5; 426/7; 800/297; 260/112.5

(56) References Cited

U.S. PATENT DOCUMENTS

| | | | |
|---|---|---|---|
| 4,315,853 A | * | 2/1982 | Fujino et al. ............. 260/112.5 |
| 4,810,504 A | * | 3/1989 | Schindler ....................... 426/7 |
| 5,934,012 A | * | 8/1999 | Holtz et al. ................... 47/1.1 |

OTHER PUBLICATIONS

Hawksworth DL et al. 1995, in Ainsworth & Bisbi's Dictionary of the Fungi, 8th Ed CAB International, University Press, Cambridge p. 616–.
Chen et al., Tremella Fuciformis; The Biology and Cultivation of Edible Mushrooms ; pp. 629, 633, and 634, 1978.*
Humfeld et al., Mushroom Mycelium Production by Submerged Propagation; Food Technology; vol. 3, No. 11, pp. 355–356, 1949.*

* cited by examiner

Primary Examiner—Bruce R. Campell
Assistant Examiner—Kent L. Bell
(74) Attorney, Agent, or Firm—Rashida A. Karmali

(57) ABSTRACT

The present invention describes new and distinct horticultural varieties of higher Basidiomycetes mushroom grown in submerged culture. Specifically, the new varieties of species of the genus Tremella offer superior yields of mushroom one-cell biomass rich in essential amino acids and vitamins and polysaccharide glucuronoxylomannan.

1 Claim, 5 Drawing Sheets

FOR HIGHER BASIDIOMYCETES MUSHROOMS GROWN (AS ONE CELL BIOMASS) IN SUBMERGED CULTURES

FIELD OF THE INVENTION

The present invention is directed to new and distinct strains of the higher Basidiomycetes edible mushroom which is adapted to grow in one cell biomass form in a submerged culture containing especially formulated nutrients.

BACKGROUND OF THE INVENTION

Higher Basidiomycetes mushrooms and toadstools have been used in folk medicine since ancient times. They include species from the Basidiomycetes class that have macroscopic fruit bodies, also known as basidioma or basidiocarp. These fruit bodies can be either hypogeous or epigeous, large enough to be seen with the naked eye, and can be picked by hand. Higher Basidiomycetes contain approximately 10,000 species from 550 genera and 80 families. The distinguishing characteristic of Basidiomycetes is the presence of basidium bearing exogenous basidiospores as a result of meiothic process.

The typical life cycle involves the germination of the basidiospore to give a primary haploid mycelium, which in turn becomes a secondary mycelium. Nuclear fusion takes place in the young basidium and meiosis takes place before basidiospore development. The macroscopic basidioma is generally fleshy and takes a variety of forms including terrestrial or hypogeneous, lignicolous or saprobic, mycorrhizal or pathogenic, edible, medicinal, hallucinogenic or poisonous mushrooms. Hawksworth D. L. et al, 1995, in Ainsworth & Bisbi's Dictionary of the Fungi, 8th ed. CAB International, University Press, Cambridge p. 616.

The most popular species of cultivated edible mushrooms include *Agaricus bisporus* (J. Lge) imbach, *A. bitorquis* (Quél) Sacc., *Lentinus edodes* (Berk.) Sing., Pleurotus spp., Auricularia spp., *Volvariella volvacea* (Fr.) Sing., *Flammulina velutipes* (Fr.) Sing, *Tremella fuciformis* Berk, *Hypsizygus marmoreus* (Peck) Bigel, *Pholita nameko* (T. Ito) S. Ito et Imai, *Grifola frondosa* (Dicks.: Fr.) S. F. Gray, *Hericium erinaceus* (Bull.: Fr.) Pers., *Dictyophora indusiata* (Vent.: Pers.) Fischer, *Stropharia rugosoannulata* Farl. apud Murr., *Lepista nuda* (Bull.: Fr.) Cooke, *Agrocybe aegerita* (Brig.) Sing.,. In 1994, the world production of cultivated edible mushrooms was estimated to be approximately five million tons, which was valued at about ten billion dollars (US).

The cultivation of fruiting bodies of mushrooms deals with living organisms, for example, the mushroom itself and other microorganisms which may either be harmful or beneficial. Therefore, the methods employed in mushroom cultivation require modifications depending upon the region being cultivated, environmental conditions and species of microorganisms encountered.

The cultivation of mushrooms for fruit bodies production is a long-term process requiring from one to several months for the first fruiting bodies to appear. The growth of pure mushroom cultures in submerged conditions on a liquid culture media permit to accelerate the speed of growth, resulting in biomass yield within a few days. Optimization of culture medium composition and physicochemical conditions of growth allow regulation of fungal metabolism in order to obtain high yield of biomass, specific mushrooms having a large amount of medicinal or other nutriceutical substances of constant composition.

SUMMARY OF THE INVENTION

The present invention is directed towards higher Basidiomycetes mushrooms grown in submerged cultures on the nutrient media. The outstanding characteristics of these higher Basidiomycetes mushrooms growing as a biomass in submerged cultures are their shorter incubation period within a few days in the nutrient media than standard fruiting Basidiomycetes mushroom varieties, and their increased yields of biologically active polysaccharide compounds such as glucuronoxylomannan-containing functional foods rich in essential amino acids and vitamins, compared with the yield of the standard fruiting Basidiomycetes mushrooms.

BRIEF DESCRIPTION OF THE ILLUSTRATIONS

Figure 1:
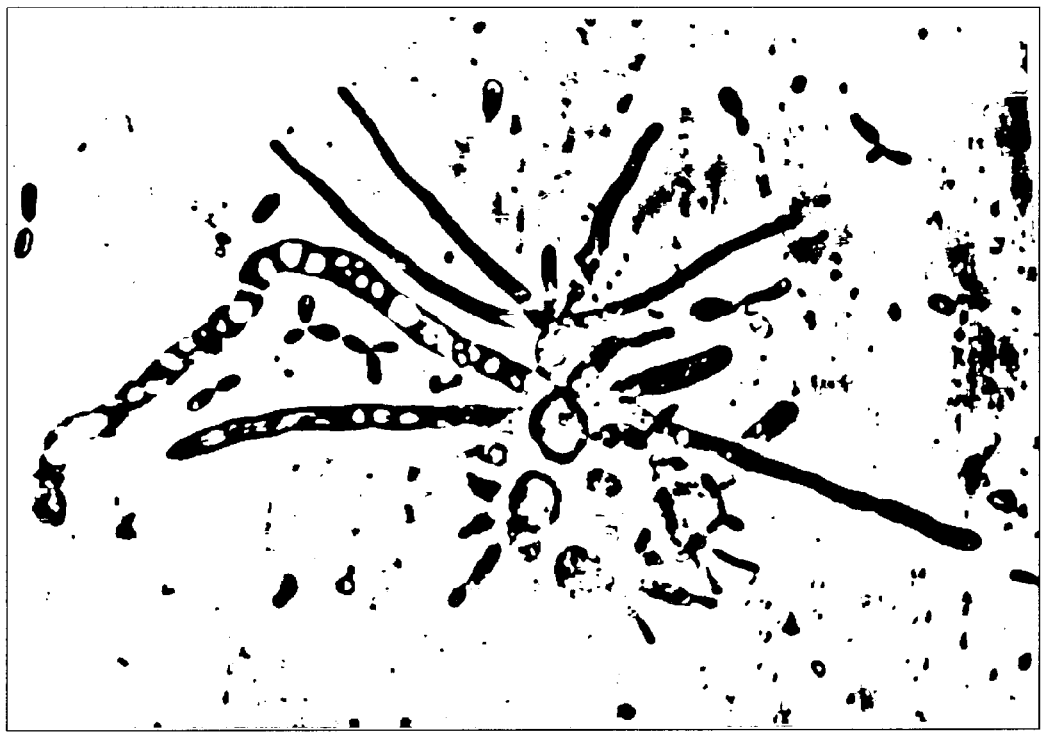
FIG. 1 shows a view of the germination of basidiospores, both by hyphae or budding cells, using an objective ×100 magnification, phase contrast.
Figure 2:
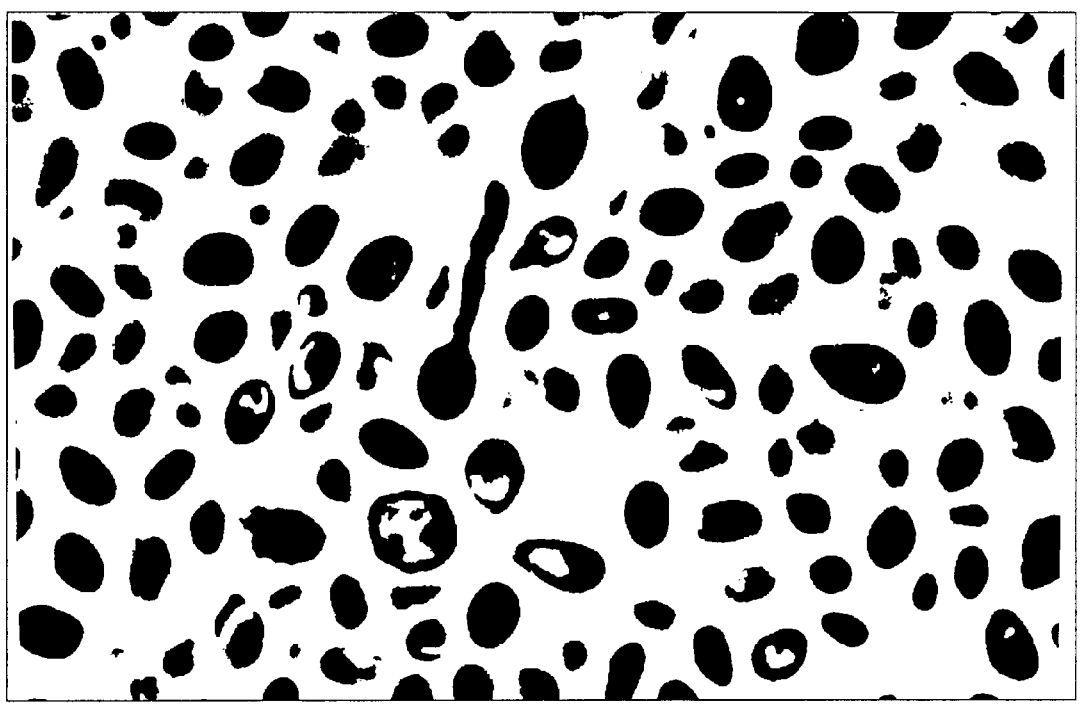
FIG. 2 shows a view of cells of haploid strain; one cell is proliferating by haploid hypha. Objective ×100, phase contrast.
Figure 3:

FIG. 3 shows a view of the preparation of *Tremella mesenterica* in Indian ink. White area around cells indicates a polysaccharide slime envelope. It is well evident, that the polysaccharide matrix around yeast-like budding cells is much more voluminous that of the hypha. Objective ×100.

Figure 4:
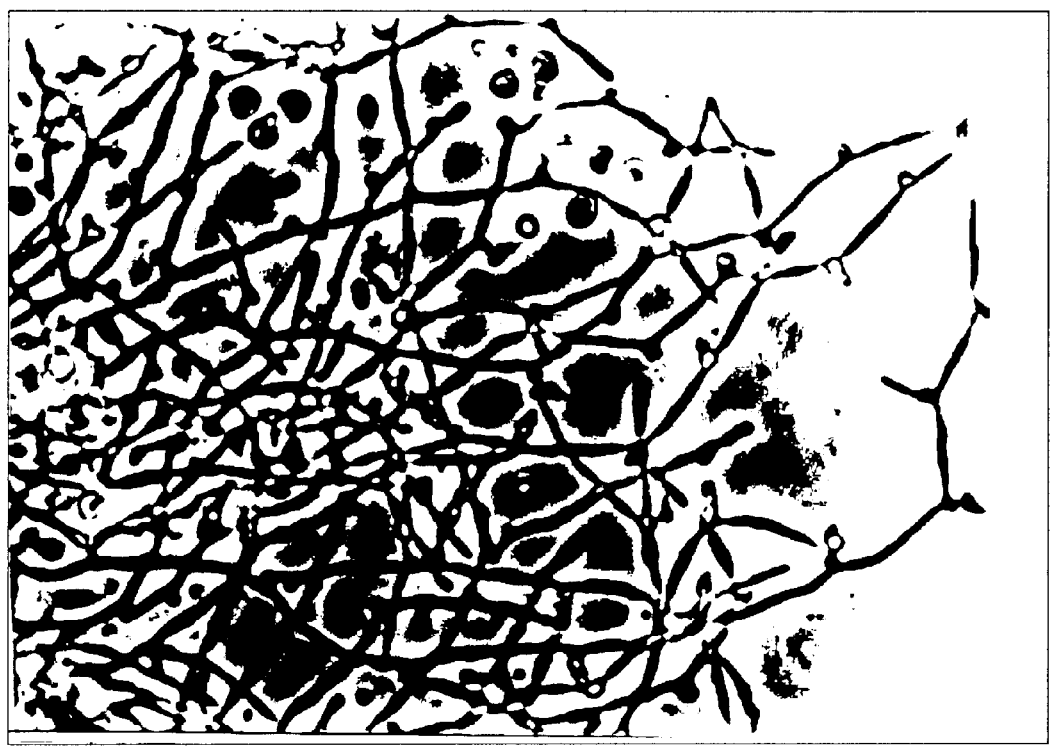

FIG. 4 shows a view of the dycariotic mycelium with clamps originating from crossed compatible haploid strains. Haploid cells are visible in the field of view. Objective ×40, phase contrast.

Figure 5:
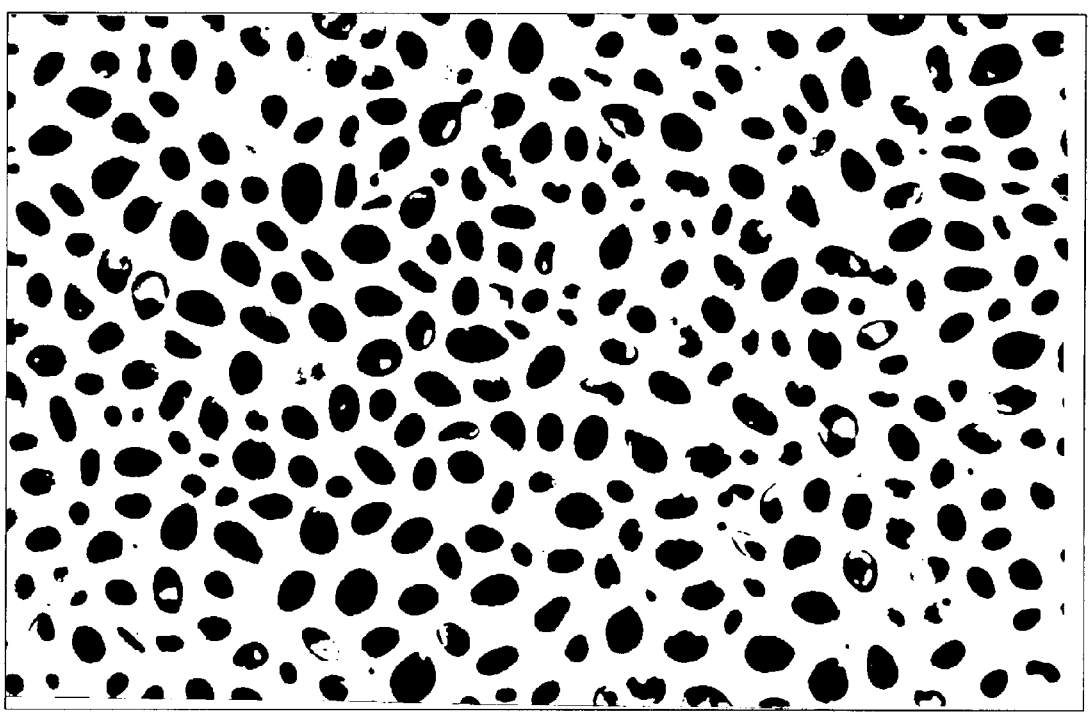

FIG. 5 shows a view of *Tremella mesenterica* CBS 101939 submerged culture. Objective ×100, phase contrast.

BOTANICAL DESCRIPTION

FIG. 1 to FIG. 5 describe the genus Tremella. The following species of the higher Basidiomycetes mushrooms has been deposited as culture with the Centraalbureau voor Schimmelcultures (CBS), Oosterstraat 1. Postbus 273, NL 3740 AG Baarn. The Netherlands, on Jun. 14, 1999: *Tremella mesenterica* as Acc. No. CBS 101939 under the Terms of the Budapest Treaty. This is a representative embodiment and in no way restricts the scope of the claims of the invention. The following descriptions are of the higher Basidiomycetes mushrooms of the genus Tremella grown in submerged cultures.

FIG. 1 to FIG. 5 describe the genus Tremella. When these Basidiomycetes mushrooms are grown under different conditions, it will be obvious that their appearance may be difficult from that described herein.

Table 1 describes the rich amino acid content of *T. mesenterica*. The biomass comprised a level of 31% of essential amino acids indicating that it is a useful source of high quality protein. In addition, the polysaccharide yield was 13.9 g/l.

TABLE 1

| | Free | | Protein | |
|---|---|---|---|---|
| Amino Acids | µg/100 mg dry weight | %, dry weight | µg/100 mg dry weight | %, dry weight |
| Aspartic acid | 42.73 | 0.043 | 2252.27 | 2.652 |
| Threonine | 138.80 | 0.139 | 1700.96 | 1.700 |
| Serine | 204.87 | 0.205 | 2281.97 | 2.281 |
| Glutamatic acid | 557.08 | 0.557 | 2020.39 | 2.020 |

TABLE 1-continued

| Amino Acids | Free | | Protein | |
|---|---|---|---|---|
| | μg/100 mg dry weight | %, dry weight | μg/100 mg dry weight | %, dry weight |
| Proline | — | — | 1379.40 | 1.379 |
| Glycine | 162.11 | 0.162 | 1929.04 | 1.929 |
| Alanine | 604.10 | 0.604 | 2402.32 | 2.402 |
| Cysteine | — | — | 294.71 | 0.294 |
| Valine | 102.40 | 0.102 | 802.71 | 0.802 |
| Methionine | 210.40 | 0.210 | — | — |
| Isoleucine | 68.46 | 0.068 | 230.23 | 0.230 |
| Leucine | 153.80 | 0.0153 | 415.59 | 0.415 |
| Tyrosine | 83.58 | 0.083 | — | — |
| Phenylalanine | 71.35 | 0.071 | — | — |
| Histidine | 87.14 | 0.087 | 290.92 | 0.290 |
| Ornitine | 41.80 | 0.042 | 187.17 | 0.187 |
| Lysine | 47.87 | 0.047 | 1876.85 | 1.576 |
| Arginine | 88.04 | 0.088 | 528.82 | 0.528 |

Among vitamins of B group, determined by microbiological method, based on the estimation of growth characteristics of sensitive auxotroph microorganism, *T. mesenterica* biomass is especially rich in niacin (Table 2).

TABLE 2

| Vitamins | Content, μg/g dry weight |
|---|---|
| Thiamine, B1 | 1.58 +/− 0.05 |
| Niacin, B5PP | 500.0 +/− 24 |
| Piridoxin, B6 | 1.0 +/− 0.01 |
| Biotine, B7 | 0.1 0.003 |

The present invention is not to be limited in scope by the embodiments disclosed in the example which is intended as an illustration of one aspect of the invention and it is contemplated that the scope of the invention encompasses any number of species and genera of the higher basidiomycetes mushrooms grown in submerged culture.

What is claimed is:

1. A new and distinct variety of Basidiomycetes mycelium grown in submerged cultures, said mycelium being of the species *Tremella mesenterica* deposited under the Budapest Treaty with Centraalbureau voor Schimmelcultures (CBS) as Accession No. CBS 101939 and comprising yeast-like budding cells of the species *Tremella mesenterica* containing a proportionately greater amount of protein, amino acids, polysaccharides and vitamins (by weight) than the respective levels in fruiting bodies of *Tremella mesenterica*.

\* \* \* \* \*